US005948797A

United States Patent [19]
LaVoie et al.

[11] Patent Number: 5,948,797
[45] Date of Patent: Sep. 7, 1999

[54] TRISBENZIMIDAZOLES USEFUL AS TOPOISOMERASE I INHIBITORS

[75] Inventors: Edmond Joseph LaVoie, Princeton Jct.; Leroy Fong Liu, Bridgewater, both of N.J.; Qun Sun, Xiao Shan, China

[73] Assignee: Rutgers, The State University Of New Jersey, Brunswick, N.J.

[21] Appl. No.: 08/782,064

[22] Filed: Jan. 13, 1997

Related U.S. Application Data

[62] Division of application No. 08/442,657, May 17, 1995, Pat. No. 5,807,874.

[51] Int. Cl.$^6$ .................................................. A61K 31/44
[52] U.S. Cl. ........................................... 514/338; 514/394
[58] Field of Search ..................................... 514/338, 394

[56] References Cited

U.S. PATENT DOCUMENTS

| Re. 26,065 | 7/1966 | Marvel et al. | 260/47 |
|---|---|---|---|
| 2,985,661 | 5/1961 | Hien et al. | 260/309 |
| 3,449,330 | 6/1969 | Guglielmetti et al. | 260/240 |
| 3,538,097 | 11/1970 | Lowe et al. | 260/268 |
| 4,938,949 | 7/1990 | Borch et al. | 424/10 |
| 5,106,863 | 4/1992 | Hajos et al. | 514/395 |
| 5,112,532 | 5/1992 | Ninomiya et al. | 252/587 |
| 5,126,351 | 6/1992 | Luzzio et al. | 514/291 |
| 5,244,903 | 9/1993 | Wall et al. | 514/279 |

OTHER PUBLICATIONS

Bathini, Y., et al., "Convenient Routes to Substituted Benzimidazoles and Imidazolo[4,5–b]pyridines Using Nitrobenzene as Oxidant", *Synthetic Communications*, 20(7), 955–963, (1990).

Chen, A.Y., et al., "A New Mammalian DNA Topoisomerase I Poison Hoechst 33342: Cytoxicity and Drug Resistance in Human Cell Cultures", *Cancer Research*, 53, 1332–1337 (Mar. 15, 1993).

Chen, A.Y., et al., "DNA Minor Groove–Binding Ligands: A Different Class of Mammalian DNA Topoisomerase I Inhibitors", *Proc. Natl. Acad. Sci., USA*, 90, 8131–8135 (Sep. 1993).

Chen, A.Y., et al., "DNA Topoisomerases: Essential Enzymes and Lethal Targets", *Annu. Rev. Pharmacol. Toxicol.*, 34, 191–218 (1994).

Cherif, A., et al., "N–(5,5–Diacetoxypent–1–yl)doxorubicin: A New Intensely Potent Doxorubicin Analogue", *J. Med. Chem.*, 35, 3208–3214, (1992).

D'arpa, P., et al., "Topoisomerase–Targeting Antitumor Drugs", *Biochimica et Biophysica Acta*, 989, 163–177 (1989).

Fox, G.J., et al., "para–Bromination of Aromatic Amines: 4–Bromo–N,N–Dimethyl–3–(Trifluoromethyl)Aniline", *Org. Syn.*, 55, 20–23, (1973).

Gallo, R.C., et al., "Studies on the Antitumor Activity, Mechanism of Action, and Cell Cycle Effects of Camptothecin", *Journal of the National Cancer Institute*, 46, 789–795 (Apr. 1971).

Gatto, B., et al., "Identification of Topoisomerase I as the Cyctotoxic Target of the Protoberberine Alkaloid Coralyne", *Cancer Res.*, 56, 2795–2800, (1996).

Giovanella, B.C., et al., "Complete Growth Inhibition of Human Cancer Xenografts in Nude Mice by Treatment with 20–(S)–Camptothecin", *Cancer Research*, 51, 3052–3055 (Jun. 1, 1991).

Iwao, M., et al., "A Regiospecific Synthesis of Carbazones via Consecutive Palladium–Catalyzed Cross–coupling and Aryne–Mediated Cyclization", *Heterocycles*, 36, 1483–1488, (1993).

Kim, J.S., et al., "Influence of steric factors on topoisomerase I inhibition and cytotoxicity of bisbenzimidazoles related to Hoechst 33342", *Abstract 4, 86th annual meeting of the American Association for Cancer Research, Toronto, Ontario, Canada*, 2689, (1995).

Kim, J.S., et al., "Influence of steric factors on topoisomerase I inhibition and cytotoxicity of bisbenzimidazoles related to Hoechst 33342", *Abstract 7, 3rd annual scientific retreat, Cancer Institute of New Jersey, Princeotn Marriott Forrestal Village*, 28, (1995).

Kim, J.S., et al., "Steric factors associated with the topoisomerase I inhibition and cytotoxicity of substituted bisbenzimidazoles", *Abstract 10, American Assn of Pharmaceutical Scientists, Eastern Regional Meeting*, 27, (1995).

Kim, J.S., et al., "Structure–activity Relationships of Benzimidazoles and Related Heterocycles as Topoisomerase I Poisons", *Bioorganic & Med. Chem.*, 4, 621–630, (1996).

Kim, J.S., et al., "Substituted 2,5'–Bi–1H–benzimidazoles: Topoisomerase I Inhibition and Cytotoxicity", *J. Med. Chem.*, 39, 992–998, (1996).

(List continued on next page.)

*Primary Examiner*—Jane Fan
*Attorney, Agent, or Firm*—Schwegman, Lundberg, Woessner & Kluth, P.A.

[57] ABSTRACT

The present invention provides anti-neoplastic topoisomerase I inhibitors of the formula:

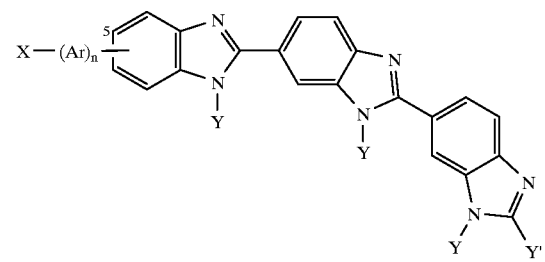

wherein Ar is ($C_6$–C12)aryl or (6- to 12-membered) heteroaryl comprising 1–3 N, S or non-peroxide O, wherein N is unsubstituted or is substituted with ($C_1$–$C_4$)alkyl; X is H, CN, CHO, OH, acetyl, $CF_3$, $OCH_3$, $NO_2$ or $NH_2$; each Y is individually H, ($C_1$–$C_4$)alkyl or aralkyl; Y' is H or ($C_1$–$C_4$) alkyl; n is 0 or 1; or a pharmaceutically acceptable salt therein.

21 Claims, 3 Drawing Sheets

OTHER PUBLICATIONS

LaVoie, E.J., et al., "Structure–activity studies related to minor groove–binding ligands which inhibit mammalian DNA topoisomerase I", *Abstract 1, 85th Annual Meeting of American Association for Cancer Research, Apr. 10–13, 1994,* San Francisco, CA, 2699, (1994).

Makhey, D., et al., "Coralyne and Related Compounds as Mammalian Topoisomerase I and Topoisomerase II Poisons", *Bioorg. & Med. Chem. Lett.,* 4, 781–791, (1996).

Makhey, D., et al., "Protoberberine Alkaloids and Related Compounds as Dual Inhibitors of Mammalian Topoisomerase I and II", *Med Chem. Res.,* 5, 1–12, (1994).

Meegalla, S.K., et al., "Synthesis and Pharmacological Evaluation of Isoindolo[1,2–b]quinazolinone and Isoindolo[2,1–a]benzimidazole Derivatives Related to the Antitumor Agent Batracylin", *J. Med. Chem.,* 37, 3434–3439, (1994).

Peters, D., et al., "Synthesis of Various 5–Substituted Uracils", *J. Heterocyclic Chem.,* 27, 2165–2173, (Nov. Dec. 19)

Pilch, D.S., et al., "Biophysical Characterization of a Cytotoxic, Topoisomerase I Poison", *Abstract 8, 3rd annual Scientific Retreat, Cancer Institute of New Jersey,* 3, (1995).

Piper, J.R., et al., "Synthesis and Antifolate Activity of 5–Methyl–5,10–dideaza Analogues of Aminopterin and Folic Acid and an Alternative Synthesis of 5,10–Dideaza-tetrahydrofolic Acid, a Potent Inhibitor of Glycinamide Ribonucleotide Formyltransferase", *J. Med. Chem.,* 31, 2164–2169, (1988).

Porai–Koshits, B.A., et al., "Imidazole derivatives Synthesis of some polybenzimidazoles", *J. GEn. Chem. USSR,* 23 as related in Chemical Abstracts, vol. 48, Nov. 10, 1954, Col. 12740, 873–9, (1953).

Porai–Koshits, B.A., et al., "Imidazole derivatives. Synthesis of some polybenzimidazoles", *Zhur. Obshchei Khim,* 23, as related from Chemical Abstracts, vol. 48, Apr. 25, 1954, Col. 4523, 835–41, (1953).

Singh, M.P., et al., "Synthesis and Sequence–Specific DNA Binding of a Topoisomerase Inhibitory Analog of Hoechst 33258 Designed for Altered Base and Sequence Recognition", *Chem. Res. Toxicol.,* 5, 597–607, (1992).

Sun, et al., *CA 123*:198740 1995.

Sun, Q., et al., "Structure activity of novel topoisomerase I inhibitors related to Hoechst 33342", *Abstract 6, American Assn of Pharmaceutical Scientists, Eastern Regional Meeting,* 25, (1995).

Sun, Q., et al., "Structure Activity of Topoisomerase I Poisons Related to Hoechst 33342", *Bioorganic & Medicinal Chemistry Letters,* 4, 2871–2876 (1994).

Sun, Q., et al., "Structure–activity studies related to minor groove–binding ligands which inhibit mammalian DNA topoisomerase I", *Cancer Institute of New Jersey, First Annual Scientific Retreat, Jun. 7, 1994,* Princeton Marriott Forrestal Village, Princeton, New Jersey, 66, (1994).

Sun, Q., et al., "Synthesis and Evaluation of Terbenzimidazoles as Topoisomerase I Inhibitors", *J.Med. Chem.,* vol. 38, pp. 3638–3644, (1995).

Sun, Q., et al., "Synthesis and pharmacological evaluation of a series of novel DNA topoisomerase I inhibitors as antitumor agents", *86th Annual meeting of the American Association for Cancer Research, Toronto, Ontario, Canada,* 2688, (1995).

Sun, Q., et al., "Synthesis and Pharmacological Evaluation of a Series of Novel DNA Topoisomerase I Inhibitors as Antitumor Agents", *Abstract 3, Scientific Proceedings of 86th Annual Meeting of the American Association for Cancer Research, Toronoto, Canada,* (Mar. 18–22, 1995).

Sun, Q., et al., "Synthesis and pharmacological evaluation of a series of novel DNA topoisomerase I inhibitors as antitumor agents", *Abstract 5, 3rd Annual Scientific Retreat, Cancer Institute of New Jersey,* 27, (1995).

Sun, Q., et al., "Synthesis of Benzimidazo[2,1–a]isoquinolines and 5,6–Dihydrobenzimidazo[2,1–a]isoquinolines", *Syn. Lett.,* submitted, (1995).

Yadagiri, B., et al., "Convenient Routes to Substituted Benzimidazoles and Imidazolo[4,5–b]Pyridines Using Nitrobenzene as Oxidant", *Synthetic Communications,* 20(7), 955–963, (1990).

TRISBENZIMIDAZOLES USEFUL AS TOPOISOMERASE I INHIBITORS

This application is a division of U.S. patent application Ser. No. 08/442,657, filed May 17, 1995 now U.S. Pat. No 5,807,874, issued Sep. 15, 1998.

BACKGROUND OF THE INVENTION

DNA topoisomerases are nuclear enzymes that control and modify the topological states of DNA by catalyzing the concerted breaking and rejoining of DNA strands. See, for example, D'Arpa et al., *Biochim. Biophys. Acta,* 989, 163 (1989). Topoisomerase II enzymes alter the topological state of DNA by means of a double strand break in the DNA. Mammalian topoisomerase II represents an effective pharmacological target for the development of cancer chemotherapeutics. (A. Y. Chen et al., *Annu. Rev. Pharmacol. Toxicol.,* 34, 191 (1994)). Among the clinical agents in use which are recognized as topoisomerase II inhibitors are etoposide (VP-16), teniposide (VM-26), mitoxantrone, m-AMSA, adriamycin (doxorubicin), ellipticine and daunomycin.

In comparison to topoisomerase II inhibitors, there are relatively few known topoisomerase I inhibitors. Camptothecin represents the most extensively studied mammalian topoisomerase I inhibitor. See R. C. Gallo et al., *J. Natl. Cancer Inst.,* 46, 789 (1971) and B. C. Giovanella et al., *Cancer Res.,* 51, 3052 (1991). The broad spectrum of potent antineoplastic activity observed for camptothecin has prompted further efforts to identify other agents which can effectively poison mammalian topoisomerase I.

It has recently been demonstrated that Hoechst 33342(1), 2'-(4-ethoxyphenyl)-5-(4-methyl-1-piperazinyl)-2,5'-bi-1H-benzimidazole, is an inhibitor of topoisomerase I.

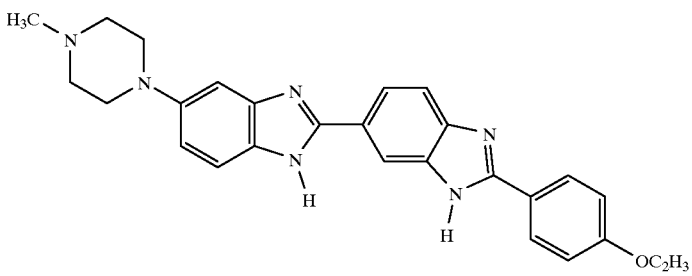

1

This agent, which binds to the minor groove of DNA, traps the reversible cleavable complex derived from DNA and topoisomerase I and produces a limited number of highly specific single-strand DNA breaks. For example, see A. Y. Chen et al., *Cancer Res.,* 53, 1332 (1993) and A. Chen et al., *PNAS,* 90, 8131 (1993). A limitation of Hoechst 33342 as an anticancer agent is the previously reported observation that it is not effective against tumor cell lines which overexpress MDR1. While KB 3-1 cells are known to be quite sensitive to Hoechst 33342, with an $IC_{50}$ of approximately 9 nM, this compound is approximately 130-fold less cytotoxic to KB V-1 cells, which are known to overexpress MDR1. Recently, several analogs of this bisbenzimidazole have been synthesized, to further investigate the structure activity relationships associated with their potency as topoisomerase I inhibitors and the related cytotoxicity. For example, Q. Sun et al., *Biorg. and Med. Chem. Lett.,* 4, 2871 (1994) disclosed the preparation of bis-benzamidazoles of formula (2):

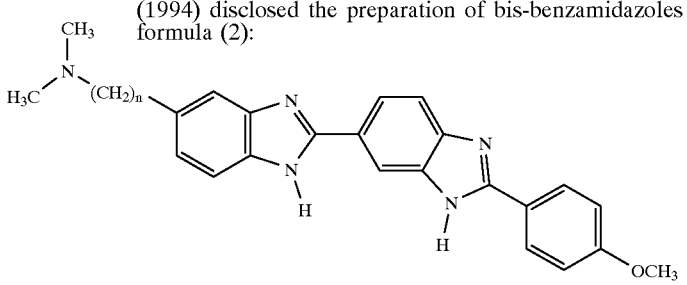

where n is 0, 1, 2, or 3. However, these compounds were found to be about one order of magnitude less cytotoxic than Hoechst 33342. Therefore, a continuing need exists for new compounds that can induce DNA cleavage in the presence of mammalian topoisomerase I.

SUMMARY OF THE INVENTION

The present invention provides a compound of general formula (I):

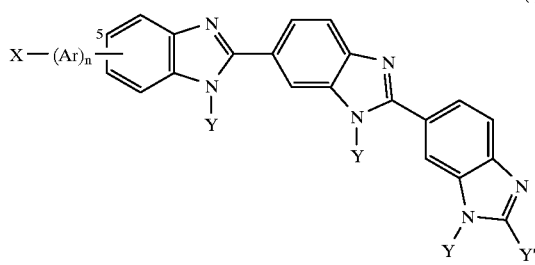

(I)

wherein Ar is aryl or a nitrogen-, sulfur- or oxygen-containing heteroaromatic group, X is H, CN, CHO, OH, acetyl, $CF_3$, $O(C_1-C_4)$alkyl. $NO_2$ or $NH_2$; each Y is individually H, $(C_1-C_4)$alkyl or aralkyl; Y' is H or $(C_1-C_4)$alkyl; n is 0 or 1; or a pharmaceutically acceptable salt thereof. Preferably, Ar is a $(C_6-C_{12})$aryl or a 5- to 12-membered heteroaryl group comprising 1–3 N, S or non-peroxide O atoms in the ring, wherein each N is unsubstituted or is substituted with $(C_1-C_4)$alkyl. As drawn, the Ar-group can occupy any position of the benzo moiety, i.e., positions 4–7, and X can occupy any available position on Ar. When Ar is phenyl, preferably X is H or is a 4- substituent.

Preferably n is 1. When n is 0, X is preferably H, CN, or CHO. Y is preferably H or $CH_3$. Y' is preferably H or $CH_3$.

Compounds of formula (I) are inhibitors of topoisomerase I, as demonstrated by their ability to promote DNA cleavage in the presence of topoisomerase I. Furthermore, compounds of formula (I) also are cytotoxic to mammalian tumor cells, including camptothecin-sensitive and camptothecin-resistant tumor cells and tumor cell lines exhibiting multi-drug resistance due to expression of the P-glycoprotein.

Therefore, the present invention also provides a method for the inhibition of mammalian tumor cell growth, comprising contacting a susceptible population of tumor cells with an effective growth-inhibiting amount of a compound of formula (I), preferably in combination with a pharmaceutically acceptable carrier. The growth of the tumor cells can be inhibited in vitro, or vivo, by administering the compound of formula (I) to a mammal in need of such treatment, such as a human cancer patient afflicted with a leukemia or solid tumor. The compounds of formula I can also be used to evaluate the activity of topoisomerase I obtained from different sources, and are expected to exhibit at least some of the other bioactivities observed for topoisomerase inhibitors, such as antibacterial, antifungal, antiprotozoal, antihelmintic and/or antiviral activity. For example, compound 14, shown on FIG. 1, exhibits antifungal activity.

DETAILED DESCRIPTION OF THE INVENTION

The aryl groups (Ar) useful in the present compounds comprise $(C_6-C_{18})$aryl, preferably $(C_6-C_{14})$ aryl, e.g., systems containing aromatic rings, which systems comprise a total of 6 to 12 carbon atoms. Thus, as used herein, the term "aryl" includes mono- or bis-$(C_1-C_4)$alkyl-substituted aryl, such as tolyl and xylyl; ar$(C_1-C_4)$alkyl, such as benzyl or phenethyl; and alkaralkyl. Preferably aryl is phenyl, benzyl or naphthyl.

Heteroaromatic rings include aromatic rings containing up to 3 ring heteroatoms such as N. S or non-peroxide O, and up to 12 ring atoms. Representative aromatic rings include thiophene, benzothiophene, naphthothiophene, trianthrene, furan, benzofuran, isobenzofuran, pyran, chromene, xanthene, phenoxathiin, pyrrole, imidazole, pyrazole, pyridine, pyrazine, triazole, tetrazole, pyrazine, triazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, phenanthroline, phenazine, isothiazole, phenothiazine, oxazole, isoxazole, furazan, phenoxazine and the like. Preferred heteroaromatic rings have a 5- or 6-membered heteroaromatic ring which may or may not be fused to an aromatic ring such as a benzo ring, e.g., the preferred 2-, 3- or 4-pyridyl substituents.

The term "alkyl" includes straight-chain or branched alkyl, as well as cycloalkyl and (cyloalkyl)alkyl, e.g., methyl, ethyl, i-propyl, cyclopropyl or cyclopropylmethyl.

Pharmaceutically acceptable salts include the acid addition salts of basic NH with organic or inorganic acids, e.g., hydrochloride, carbonate, sulfate, acetate, phosphate, tartarate, citrate, malate, maleate, propionate, and the like.

Figure 1:
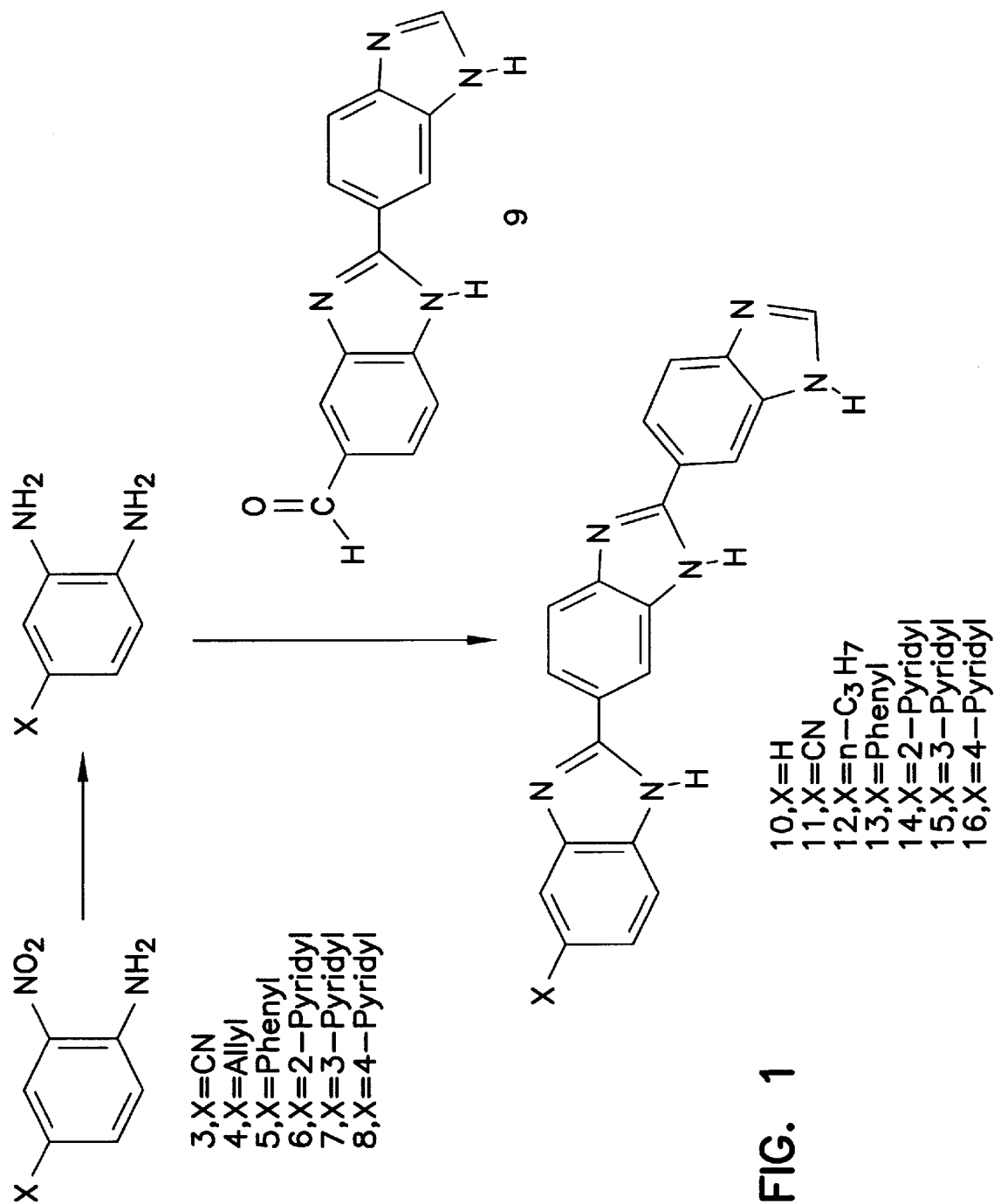
FIG. 1 is a schematic depiction of the synthesis of compounds 10–16.

The preparation of representative substituted trisbenzimidazoles is outlined in FIG. 1. With the exception of phenylenediamine which was commercially available, the appropriately substituted phenylenediamines were synthesized by catalytic hydrogenation of the respective o-nitroaniline derivatives. These phenylenediamines were then coupled with 5-formyl-2-(benzimidazo-5'-yl) benzimidazole, 9, by heating in nitrobenzene at 150° C. to provide the various trisbenzimidazoles, 10–16, in yields ranging from 43–96%, employing the general methodologies of M. P. Singh et al., *Chem. Res. Toxicol.*, 5, 597 (1992) and Y. Bathini et al., *Synth Comm.*, 20, 955 (1990).

Figure 2:
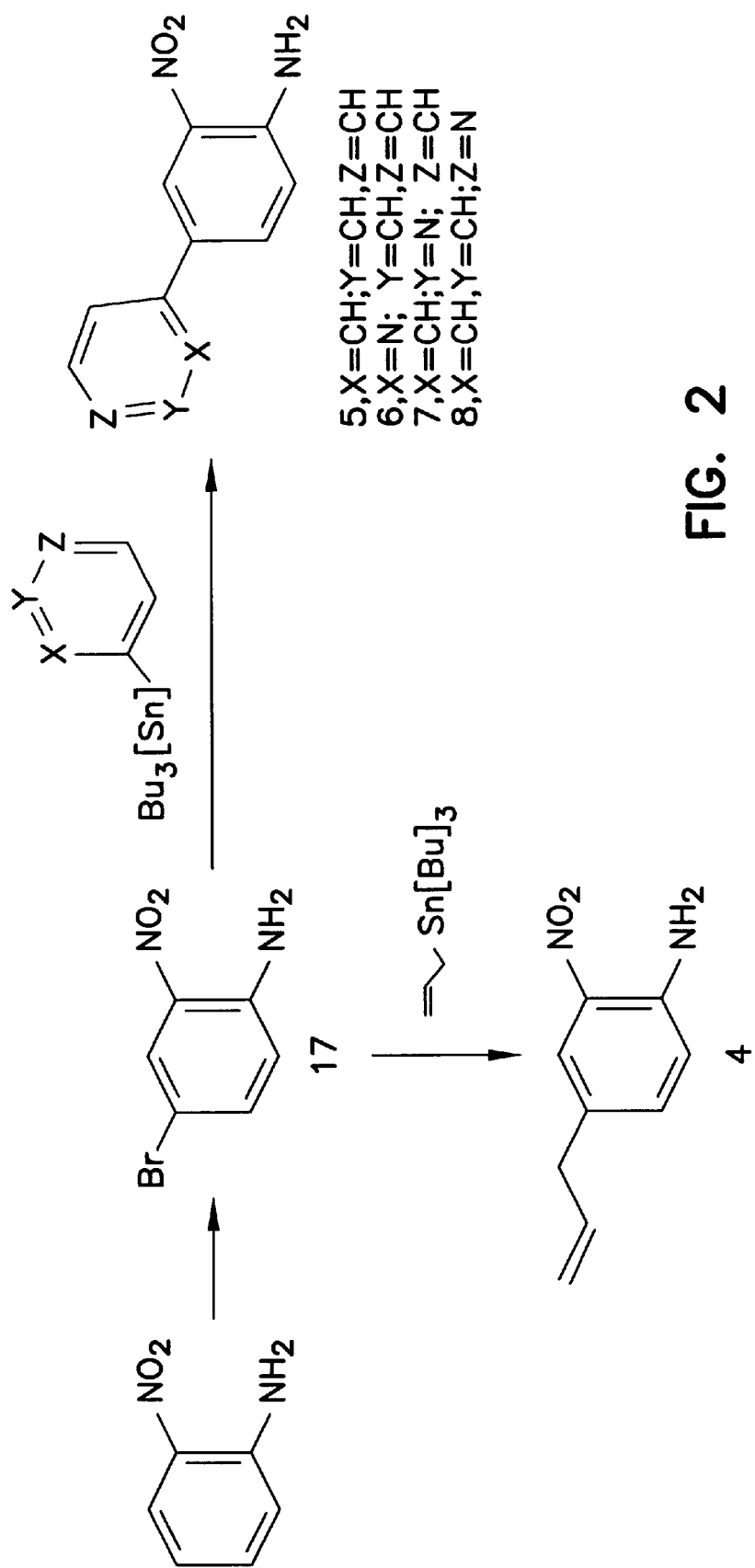
FIG. 2 is a schematic depiction of the preparation of intermediates 4–8 used to prepare compounds of the invention.

The requisite nitroanilines, as outlined in FIG. 1, with the exception of 3 which was commercially available, were synthesized from 4-bromo-2-nitroaniline, 17. Compound 17 was prepared from o-nitroaniline in good yield, 94%, using 2,4,4,6-tetrabromo-2,5-cyclohexadienone as the bromination reagent. G. J. Fox et al., *Org. Syn.*, 55, 20 (1973). While allyltributyltin and phenyltributyltin are commercially available, the pyridyltributyltin derivatives were prepared from tributyltin chloride and 2-, 3-, and 4-bromopyridine, respectively. See D. Peters et al., *Heterocyclic Chem.*, 27, 2165 (1990). These tributyltin derivatives were then coupled with 4-bromo-2-nitroaniline using $PdCl_2(PPh_3)_2$ as the catalyst in DMF as outlined in FIG. 2 to provide compounds 4, 5, 6, 7, and 8, respectively, in accord with the methodology of M. Iwao et al., *Heterocycles,* 36, 1483 (1993). This methodology can generally be applied to prepare 3-, 4-, 5- or 6-aryl- and heteroaryl-substituted 2-nitroanilines from the corresponding bromonitroanilines.

Figure 3:
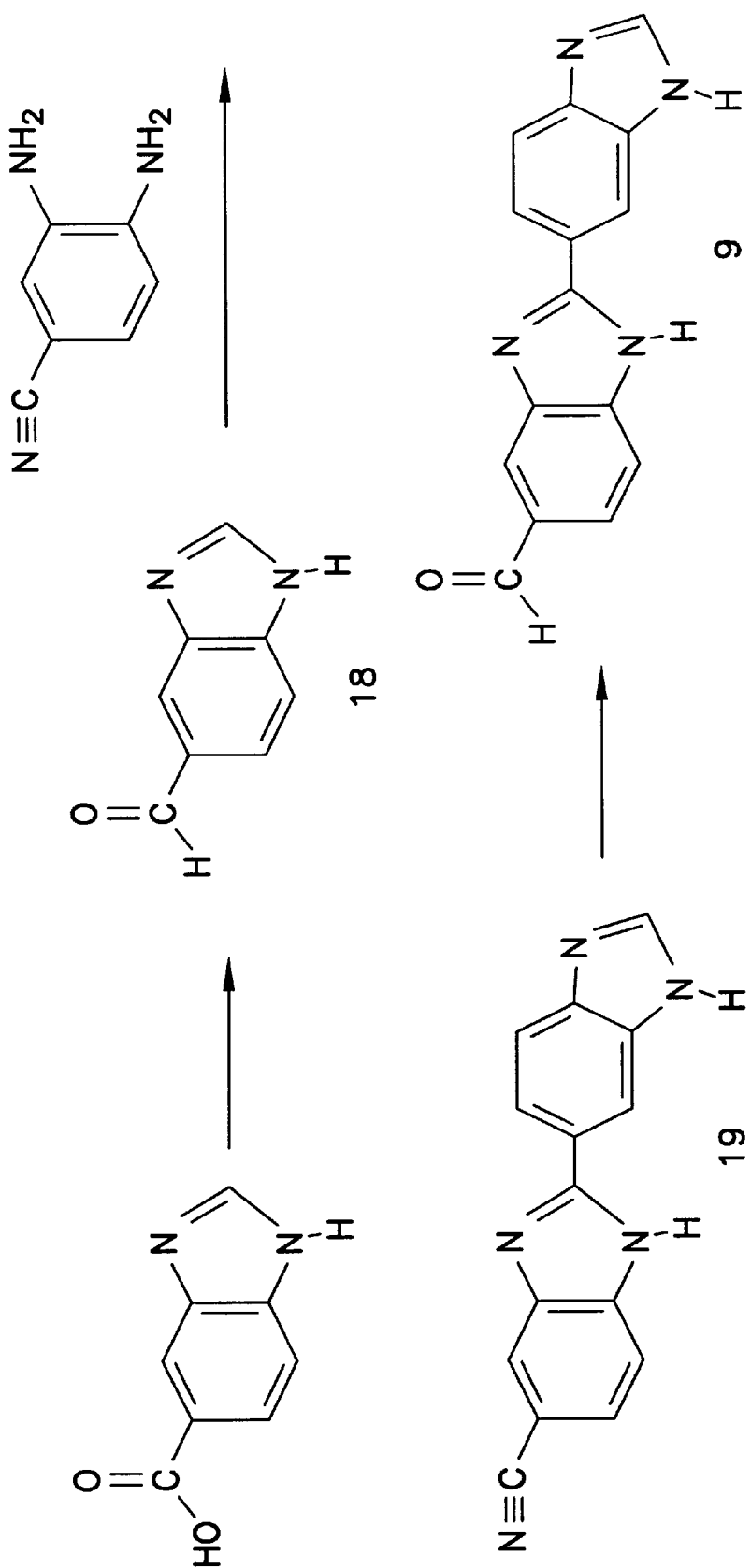
FIG. 3 is a schematic depiction of the preparation of intermediate 9.

The preparation of 5-formyl-2-(benzimidazo-5'-yl) benzimidazole, 9, was accomplished as outlined in FIG. 3. Reduction of 5-benzimidazolecarboxylic acid to 5-hydroxymethylbenzimidazole was accomplished using LiAlH$_4$. Oxidation of the resulting crude benzylic alcohol with tetrapropylammonium perruthenate (TPAP) and N-methylmorpholine N-oxide provided in two steps the desired 5-formylbenzimidazole in 32% an overall yield. See, A. Cherif et al., *J. Med. Chem.,* 35, 3208 (1992). Coupling of 5-formylbenzimidazole with 4-cyano-1,2-phenylenediamine provided 5-cyano-2-(benzimidazol-5'-yl) benzimidazole, 19, which when treated with Ni-Al catalyst in the presence of aqueous formic acid gave 5-formyl-2-(benzimidazol-5'-yl)benzimidazole, 9, in 65% yield. (J. R. Pipier et al., *J. Med. Chem.,* 31, 2164 (1988)).

The compounds of the present invention can be formulated as pharmaceutical compositions and administered to a mammalian host, such as a human cancer patient, in a variety of forms adapted to the chosen route of administration, i.e., orally or parenterally, by intravenously, intramuscularly or subcutaneous routes.

Thus, the present phosphoramidate compounds may be orally administered, for example, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavoring agent such as peppermint, oil of wintergreen, or cherry flavoring may be added. When the unit dosage form is a capsule, it may contain in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion use can include sterile aqueous solutions or dispersions or sterile powders comprising the active ingredient which are adapted for the extemporaneous preparation of sterile injectable or infusable solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, and liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersion or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freezedrying techniques, which yield a powder of the active ingredient plus any additional desired ingredient present in the previously sterile-filtered solutions.

Useful dosages of the compounds of 1 can be determined by comparing their in vitro activity, and in vivo activity in animal models, to that of an equivalent dosage of camptothecin (see, for example, B. C. Giovanella et al., *Cancer Res.,* 51, 3052 (1991)) or Hoechst 33342 (see, A. Y. Chen et al., *Cancer Res.,* 53, 1332 (1993)). Methods for the extrapolation of effective anti-tumor dosages in mice, and other animals, to humans are known to the art; for example, see U.S. Pat. No. 4,938,949.

The present analogs can be used to treat cancers known to be susceptible to topoisomerase I inhibitors, including, but not limited to, Burkitt's tumor, chronic lymphocytic leukemia, multiple myeloma, squamous cell and large cell anaplastic carcinomas, adenocarcinoma of the lung, Ewing's sarcoma, non-Hodgkins lymphoma, breast tumor, colon tumor, stomach tumor, oat-cell bronchogenic carcinoma, squamous cell carcinoma of the cervix, ovarian tumors, bladder tumors, testicular tumors, endometrial tumors, malignant melanoma and acute lymphocytic leukemia, and prostatic carcinoma. The present compounds can be administered as single agents, or in combination with other antineoplastic drugs commonly employed to treat these cancers.

The invention will be further described by reference to the following detailed examples, wherein melting points were determined with a Thomas-Hoover unimelt capillary melting point apparatus. Infrared spectral data (IR) were obtained on a Perkin-Elmer 1600 Fourier transform spectrophotometer and are reported in $cm^{-1}$. Proton ($^1$H NMR) and carbon ($^{13}$C NMR) nuclear magnetic resonance were recorded on a Varian Gemini-200 Fourier Transform spectrometer. NMR spectra (200 MHz $^1$H and 50 MHz $^{13}$C) were recorded in $CDCl_3$ (unless otherwise noted) with chemical shifts reported in δ units downfield from tetramethylsilane (TMS). Coupling constants are reported in hertz. Mass spectra were obtained from Midwest Center for Mass Spectrometry within the Department of Chemistry at the University of Nebraska-Lincoln. Combustion analyses were performed by Atlantic Microlabs, Inc., Norcross, Ga., and were with in ±0.4%. THF was freshly distilled form sodium and benzophenone prior to use. Allyltributyltin and phenyltributyltin were purchased from Aldrich Chemical Company.

EXAMPLE 1

General Procedure for $PdCl_2(PPh_3)_2$-catalyzed Coupling Reaction of 4-Bromo-2-nitroaniline (13) with Tin Compounds (A) 4-Phenyl-2-nitroaniline (5).

A solution of 4-bromo-2-nitroaniline 17 (1.0 g, 4.67 mmol), tributylphenyl tin (2.2 g, 6.07 mmol), bis(triphenylphosphine)palladium (II) chloride (164 mg, 0.234 mmol), and triphenylphosphine (613 mg, 2.34 mmol) in DMF (15 ml) was heated under $N_2$ at 120° C. overnight. After the solution was cooled to room temperature, the reaction mixture was directly chromatographed on silica gel eluting with 2–5% EtOAc/Hexane to give 752 mg (75%) of 5 as a yellow solid: mp 169–171° C.; IR ($CHCl_3$) 3517, 3398, 3022, 1635, 1525, 1250; $^1$H NMR δ 8.38 (1H, d, J=2.2), 7.66 (1H, dd, J=8.7, 2.2), 7.59–7.54 (2H, m), 7.49–7.34 (3H, m), 6.90 (1H, d, J=8.8), 6.13 (NH, brs); $^{13}$C NMR δ 144.2, 139.3, 135.0, 130.9, 129.5, 127.8, 126.8. 124.4, 119.8, 112.8; Anal. Calcd for $C_{12}H_{10}N_2O_2$: C, 67.28; H, 4.70; N, 13.08. Found: C, 67.38, H, 4.76; N, 13.01.

(B) 4-Allyl-2-nitroaniline (4).

Prepared from 4-bromo-2-nitroaniline 17 (1.70 g. 7.84 mmol) and allyltributyltin (3.38 g, 10.2 mmol) as a yellow solid in 96% yield as described above for 5: mp 29–31° C.; IR (KBr) 3490, 3374, 1638, 1518, 1341, 1253; $^1$H NMR δ 7.90 (1H, d, J=2.0), 7.19 (1H, dd, J=8.5, 2.0), 6.77 (1H, d, J=8,5), 6.05 (NH, brs), 6.00–5.80 (1H, m), 5.11 (1H, dd, J=1.4, 1.4), 5.04 (1H, ddd, J=6.6, 3.0. 1.5), 3.28 (1H, d, J=6.6); $^{13}$C NMR δ 143.81, 137.13, 129.34, 125.59, 119.49, 116.95, 39.18; HRMS (EI) calcd for $C_9H_{10}N_2O_2$ 178.0742, found 178.0746.

(C) 4-(2'-Pyridyl)-2-nitroaniline (6).

Prepared from 4-bromo-2-nitroaniline 17 (597 mg, 2.75 mmol) and 2-tributylstannylpyridine (1.01 g, 2.75 mmol) as a yellow solid in 52% yield as described above for 5: mp 146–148° C.; IR ($CHCl_3$) 3516, 3397, 3020, 1634, 1524, 1341, 1250; $^1$H NMR δ 8.74 (1H, d, J=2.2), 8.63 (1H, dd, J=4.9, 1.5), 8.13 (1H, dd, J=8.8, 2.1), 7.78–7.66 (2H, m), 7.20 (1H, ddd, J=4.8, 4.7. 1.9), 6.92 (1H, d, J=8.8), 6.37 (NH, brs); $^{13}$C NMR δ 155.6, 150.1, 145.6, 137.4, 134.5, 129.1, 124.7, 122.4, 119.8, 119.7; Anal. Calcd for $C_{11}H_9N_3O_2$: C, 61.39; H, 4.21; N, 19.53. Found: C, 61.29; H, 4.23; N, 19.43.

(D) 4-(3'-Pyridyl)-2-nitroaniline (7).

Prepared from 4-bromo-2-nitroaniline 17 (1.42 g, 6.53 mmol) and 3-tributylstannylpyridine (3.60 g, 9.79 mmol) as a yellow solid in 32% yield as described above for 5: mp 177–179° C.; IR ($CHCl_3$) 3515, 3399, 3052, 2983, 1638, 1524, 1341, 1259; $^1$H NMR δ 8.68 (1H, d, J=1.7), 8.42 (1H, dd, J=4.8, 1.5), 8.22 (1H, d, J=2.2), 7.74 (1H, ddd, J=7.9, 2.4, 1.6), 7.50 (1H, dd, J=8.7, 2.2), 7.23 (1H, ddd, J=8.0, 4.8, 0.8), 6.92 (1H, d, J=8.8), 6.56 (NH, brs); $^{13}$C NMR δ 148.7, 147.8, 145.4, 135.0, 134.4, 133.8, 126.5, 124.4, 124.0, 120.4; Anal. Calcd for $C_{11}H_9N_3O_2$: C, 61.39; H, 4.21: N, 19.53. Found: C, 61.28; H, 4.16; N, 19.40.

(E) 4-(4'-Pyridyl)-2-nitroaniline (8).

Prepared from 4-bromo-2-nitroaniline 17 (165 mg, 0.76 mmol) and 4-tributylstannylpyridine (280 mg, 0.76 mmol) as a yellow solid in 25% yield as described above for 5: mp 230–232° C.; IR ($CHCl_3$) 3518, 3398, 3032, 1636, 1528, 1344; $^1$H NMR ($CD_3OD$) δ 8.55 (2H, d, J=6.3), 8.52 (1H, d, J=2.3), 7.84 (1H, dd, J=8.9, 2.3), 7.71 (2H, d, J=6.4), 7.13 (1H, d, J=8.9); $^{13}$C NMR ($CD_3OD$) δ 149.4, 133.4, 124.0, 120.7, 120.0; HRMS (EI) calcd for $C_{11}H_9N_3O_2$ 215.0695, found 215.0698.

EXAMPLE 2

5-Formyl-2-(benzimidazol-5'-yl)benzimidazole (9)

A mixture of 5-cyano-2-(benzimidazol-5'-yl) benzimidazole 19 (148 mg, 0.57 mmol), Ni-Al catalyst (500 mg), formic acid (7 ml) and water (3 ml) was heated under refluxed under $N_2$ for 4h. The hot reaction mixture was immediately filtered through a plug of celite, and evaporated to give a yellow solid. The yellow solid was then dissolved in hot water (5 ml), and the solution was neutralized to pH 9 by 2N NaOH. The solid precipitated was collected by suction filtration and further purified by flash chromatography on silica gel (15% MeOH/EtOAc) to give 142 mg (95%) of 9 as a white solid: mp>275° C.; IR (KBr) 3106, 2835, 1685, 1618, 1432, 1293; $^1$H NMR ($CD_3OD$) δ 10.01 (1H, s), 8.39 (1H, s), 8.35 (1H, s), 8.13 (1H, s), 8.06 (1H, dd, J=8.6, 1.6), 7.83 (1H, dd, J=8.4, 1.4), 7.77 (1H, d, J=8.5), 7.71 (1H, d, J=8.3); HRMS (FAB) calcd for $C_{15}H_{11}N_4O$ 263.0933, found 263.0932.

EXAMPLE 3

General Procedures for Preparing 5-Substituted Trisbenzimidazoles.

(A) 2-[2'-(Benzimidazol-5"-yl)benzimidazol-5'-yl]benzimidazole (10).

A mixture of 5-formyl-2-(benzimidazol-5'-yl) benzimidazole 9 (121 mg, 0.46 mmol) and phenylenediamine (60 mg, 0.55 mmol) in nitrobenzene (8 ml) was heated at 150° C. under $N_2$ overnight. The mixture was cooled to room temperature and chromatographed on silica gel (0–20% MeOH/EtOAc) to afford 155 mg (96%) of 10 as a solid: mp>275° C.; IR (KBr) 3400, 3157, 1630, 1542, 1438, 1294; $^1$H NMR (DMSO-$d_6$+3 drops of CF$_3$COOH) δ 9.71 (1H, s), 8.75 (1H, s), 8.65 (1H, d, J=1.1), 8.48 (1H, dd, J=8.7, 1.5), 8.21 (1H, dd, J=8.6, 1.6), 8.14 (1H, d, J=8.8), 8.08 (1H, d, J=8.7), 7.90 (2H, dd, J=6.2, 3.1), 7.61 (2H, dd, J=6.1, 3.1); $^{13}$C NMR (DMSO-$d_6$+3 drops of CF$_3$COOH) δ 154.4, 149.8, 133.2, 132.0, 131.7, 126.2, 125.5, 125.4, 123.9, 123.6, 116.3, 115.9, 114.23, 114.17, 114.13; HRMS (FAB) calcd for $C_{21}H_{15}N_6$ 351.1358, found 351.1367.

(B) 5-Cyano-2-[2'-(benzimidazol-5"-yl)benzimidazol-5'-yl] benzimidazole (11).

Hydrogenation of 3 (70 mg, 0.43 mmol) was accomplished at 40 psi H$_2$ at room temperature for 1 h using 10% Pd-C (30 mg) in EtOAc (10 ml). The reaction mixture was filtered and concentrated in vacuo to afford a solid. The solution of this solid and 9 (87 mg, 0.33 mmol) in nitrobenzene (5 ml) was heated at 150° C. under N$_2$ overnight. The mixture was cooled to room temperature, and chromatographed directly on silica gel (0–10% MeOH/EtOAc) to give 107 mg (86%) of 11 as a solid; mp>280° C.; IR (KBr) 3416, 3148, 2222, 1626, 1553, 1441, 1292; $^1$H NMR (DMSO-$d_6$+3 drops of CF$_3$COOH) δ 8.50 (1H, s), 8.46 (1H, s), 8.40 (1H, s), 8.18–8.11 (3H, m), 7.81–7.75 (3H, m), 7.62 (1H, dd, J=8.3, 1.5); HRMS (FAB) calcd for $C_{22}H_{13}N_7$ 376.1310, found 376.1309.

(C) 5-Propyl-2-[2'-(benzimidazol-5"-yl)benzimidazol-5'-yl] benzimidazole (12).

Prepared from 4-allyl-2-nitroaniline 4 (312 mg, 1.75 mmol) and 5-formyl-2-(benzimidazol-5'-yl)benzimidazole 9 (121 mg, 0.46 mmol) in 79% yield as described above for 11: solid; mp>270° C.; IR (KBr) 3421, 3068, 2957, 1434; $^1$H NMR (DMSO-$d_6$+3 drops of CF$_3$COOH) δ 9.66 (1H, s), 8.73 (1H, s), 8.59 (1H, s), 8.48 (1H, dd, J=8.7, 1.5), 8.13 (1H, dd, J=8.7, 1.4), 8.11 (1H, d, J=8.7), 8.02 (1H, d, J=8.5), 7.79 (1H, d, J=8.4), 7.66 (1H, s), 7.45 (1H, dd, J=8.5, 1.3), 2.80 (2H, t, J=7.0), 1.70 (2H, m), 0.96 (3H, t, J=7.2); $^{13}$C NMR (DMSO-$d_6$+3 drops of CF$_3$COOH) δ 153.84, 149.74, 141.64, 141.01, 139.37, 133.10, 132.26, 131.99, 130.34, 127.08, 126.26, 125.14, 141.64, 141.01, 139.37, 133.10, 132.26, 131.99, 130.34, 127.08, 126.26, 125.14, 122.91, 117.52, 116.32, 116.06, 115.76, 113.78, 112.99, 37.45, 24.73, 13.74;

(D) 5-Phenyl-2-[2'(benzimidazol-5"-yl)benzimidazol-5'-yl] benzimidazole (13).

Prepared from 4-phenyl-2-nitroaniline 5 (247 mg, 1.15 mmol) and 5-formyl-2-(benzimidazol-5'-yl)benzimidazole 9 (201 mg, 0.77 mmol) in 89% yield as described for 11: solid; mp262–164° C. dec; IR (KBr) 3402, 3104, 1627, 1552, 1442, 1290; $^1$H NMR (DMSO-$d_6$+3 drops of CF$_3$COOH) δ 9.66 (1H, s), 8.74 (1H,. s), 8.65 (1H, s), 8.50 (1H, dd, J =8.8, 1.1), 8.21 (1H, dd, J=8.7, 1.4), 8.12 (1H, d, J=8.8), 8.06 (1H,s), 8.05 (1H, d, J=8.4), 7.97 (1H, d, J=8.7), 7.89 (1H, dd, J=8.7, 1.5), 7.80 (2H, d, J=7.0), 7.61–7.47 (3H, m); HRMS (FAB) calcd for $C_{27}H_{19}N_6$ 427.1671, found 427.1666.

(E) 5-(2-Pyridyl)-2-[2'-(benzimidazol-5"-yl)benzimidazol-5'-yl]benzimidazole (14).

Prepared from 4-(2'-pyridyl)-2-nitroaniline, 6 (110 mg, 0.50 mmol), and 5-formyl-2-(benzimidazol-5'-yl) benzimidazole 9 (51 mg, 0.25 mmol) in 84% yield as described above for 11: solid; mp>275° C.; IR (KBr) 3411, 3157, 1630, 1593, 1432; $^1$H NMR (CD$_3$OD) δ 8.59 (1H, d, J=4.8), 8.35 (1H, s), 8.31–8.25 (2H, m), 8.10 (1H, s), 8.04–7.94 (2H, m), 7.85–7.77 (3H, m), 7.72 (1H, d, J=8.6), 7.68 (1H, d, J=8.7), 7.64 (1H, d, J=8.7), 7.30 (1H, m); HRMS (FAB) calcd for $C_{26}H_{18}N_7$ 428.1624, found 428.1611.

(F) 5-(3-Pyridyl)-2-[2'-(benzimidazol-5"-yl)benzimidazol-5'-yl]benzimidazole (15).

Prepared from 4-(3'-pyridyl)-2-nitroaniline 7 (183 mg, 0.85 mmol) and 5-formyl-2-(benzimidazol-5'-yl) benzimidazole 9 in 46% yield as described above for 11: solid; mp>275° C.; IR (KBr) 3400, 3070, 2836, 1438, 1289; $^1$H NMR (CD$_3$OD) ε 8.83 (1H, d, J=1.6), 8.49 (1H, dd, J=4.9, 1.5), 8.38 (1H, d, J=1.1), 8.31 (1H, d, J=1.1), 8.29 (1H, s), 8.11 (1H, ddd, J=8.0, 2.3, 1.6), 8.05 (1H, dd, J=8.5, 1.6), 8.00 (1H, dd, J=8.5, 1.6), 7.81 (1H, d, J=1.1), 7.77–7.68 (3H, m), 7.55–7.47 (2H, m); HRMS (FAB) calcd for $C_{26}H_{18}N_7$ 428.1624, found 428.1612.

(G) 5-(4-Pyridyl)-2-[2'-(benzimidazol-5"-yl)benzimidazol-5'-yl]benzimidazole (16).

Prepared from 4-(4'-pyridyl)-2-nitroaniline 8 (35 mg, 0.16 mmol) and 5-formyl-2-(benzimidazol-5'-yl)benzimidazole 9 (50 mg, 0.19 mmol) in 43% yield as described above for 11: solid; mp>280° C.; IR (KBr) 3411, 3118, 1600, 1552, 1439, 1290; $^1$H NMR (CD$_3$OD) δ 8.51 (2H, d, J=6.2), 8.33 (1H, d, J=1.1), 8.27 (1H, s), 8.25 (1H, d, J=1.1), 8.01 (1H, dd, J=8.6, 1.7), 7.96 (1H, dd, J=8.9, 2.0), 7.87 (1H, d, J=1.0), 7.74–7.56 (6H, m); HRMS (FAB) calcd for $C_{26}H_{18}N_7$ 428.1624, found 428.1625.

EXAMPLE 4

4-Bromo-2-nitroaniline (17).

A solution of 2-nitroaniline (5 g, 36.2 mmol) in CH$_2$Cl$_2$ (100 ml) was cooled to −10° C., and treated by 90% 2,4,4,6-tetrabromo-2,5-cyclohexadienone (19.8 g, 43.5 mmol) in 5 portions. The mixture was stirred at −10° C.–0° C. for 1 hr. After being warmed to room temperature, the reaction mixture was washed by 2N NaOH (60 ml) and brine (50 ml), dried over Na$_2$SO$_4$ and evaporated. Flash chromatography on silica gel (5% EtOAc/Hexane) gave 7.40 g (94%) of 17 as a yellow solid: mp 109–110 (lit. mp 112–113° C.); $^1$H NMR δ 8.27 (1H, d, J=2.3), 7.43 (1H, dd, J=8.9, 2.4), 6.73 (1H, d, J=8.8), 6.09 (NH, brs).

EXAMPLE 5

5-Formylbenzimidazole (18).

A suspension of 5-benzimidazolecarboxylic acid (1.57 g, 9.7 mmol) in dry THF (50 ml) was cooled to −78° C. under N$_2$, and treated with LiAlH$_4$ (736 mg, 19.4 mmol). After the addition, the mixture was allowed to warm slowly to room temperature and then stirred at r.t. overnight. The mixture was quenched by MeOH and H$_2$O cautiously, and passed through a short silica gel column eluting with 10% MeOH/ EtOAc. The eluate was concentrated to give 876 mg crude alcohol as a solid. The crude alcohol (876 mg) was dissolved in a mixture of DMF (3 ml), THF (10 ml) and CH$_2$Cl$_2$ (40 ml). 4-Methylmorpholine N-oxide (2.25 g, 19.2 mmol), 4A molecular sieves (5 g), and TPAP (169 mg, 0.48 mmol) were subsequently added to the crude alcohol solution. The mixture was stirred at room temperature overnight, and filtered through a pad of silica gel eluting with 10% MeOH/EtOAc. The elute was concentrated and further purified by flash chromatography on silica gel eluting with 0–10% MeOH/

EtOAc to give 452 mg (32%, 2 steps) of 17 as a white solid: mp 164–166° C.; IR (KBr) 3087, 2818, 1690, 1292: $^1$H NMR (CD$_3$OD) δ 9.95 (1H, s), 8.34 (1H, s), 8.08 (1H, d, J=1.5), 7.74 (1H, dd, J=8.4, 1.5), 7.63 (1H, d, J=8.4); $^{13}$C NMR (CD$_3$OD) δ 194.2, 146.0, 143.0, 139.8, 133.6, 124.9, 120.7 116.6; Anal. Calcd for $C_8H_6N_2O$: C, 65.75: H, 4.14; N, 19.17, Found: C, 65.60: H, 4.17: N, 19.08.

EXAMPLE 6

5-Cyano-2-(benzimidazol-5'-yl)benzimidazole (19).

A mixture of 5-formylbenzimidazole 18 (211 mg, 1.44 mmol) and 4-cyano-1,2-phenylenediamine (230 mg, 1.73 mmol) in nitrobenzene (10 ml) was heated at 150° C. under $N_2$ overnight. The mixture was cooled to room temperature and directly chromatographed on silica gel eluting with 0–15% MeOH/EtOAc to give 244 mg (65%) of 18 as a solid: mp>270° C.; IR (KBr) 3110, 2826, 2224, 1627, 1426, 1294; $^1$H NMR (CD$_3$OD) δ 8.41 (1H, s), 8.33 (1H, s), 8.07 (1H, dd, J=8.6, 1.5), 7.98 (1H, s), 7.78 (1H, d, J=8.4), 7.73 (1H, d, J=8.4), 7.56 (1H, dd, J=8.4, 1.5); $^{13}$C NMR (DMSO-d$_6$+3 drops of CF$_3$COOH) δ 153.4, 140.4, 138.3, 132.9, 131.6, 127.0, 125.8, 125.3, 120.8, 119.8, 116.0, 115.8, 113.9, 105.5; HRMS (FAB) calcd for $C_{15}H_{10}N_5$ 260.0936, found 260.0935.

EXAMPLE 7

Bioassays

A. Topoisomerase I-Mediated DNA Cleavage Assays

DNA topoisomerase I was purified from calf thymus gland as reported previously by B. D. Halligan et al., *J. Biol. Chem.*, 260, 2475 (1985). Plasmid YEpG was also purified by the alkali lysis method followed by phenol deproteination and CsCl/ethidium isopycnic centrifugation as described by T. Mariatis et al., *Molecular Cloning, A Laboratory Manual*, Cold Spring Harbor Labs, NY (1982) at pages 149–185. The end-labeling of the plasmid was accomplished as previously described by L. F. Liu et al., *J. Biol. Chem.*, 258, 15365 (1983). The cleavage assays were performed as previously reported by A. Y. Chen et al., *Cancer Res.*, 53, 1332 (1993). Human topoisomerase was isolated as a recombinant fusion protein using a T7 expression system.

B. Cytotoxicity Assay

The cytotoxicity was determined using the as MTT-microtiter plate tetrazolinium cytotoxicity assay (MTA) following the procedures of F. Denizot et al., *J. Immunol. Methods*, 89, 271 (1986); J. Carmichael et al., *Cancer Res.*, 47, 936 (1987) and T. J. Mosmann et al., *Immunol. Methods*, 65, 55 (1983). The human lymphoblast RPMI 8402 and its camotothecin-resistant variant cell line, CPT-K5 were provided by Dr. Toshiwo Andoh (Aichi Cancer Center Research Institute, Nagoya, Japan). See, for example, T. Andoh et al., *Adv. Pharmacol.*, 29B, 93 (1994). The cytotoxicity assay was performed using 96-well microtiter plates. Cells were grown in suspension at 37° C. in 5% $CO_2$ and maintained by regular passage in RPMI medium supplemented with 10% heat inactivated fetal bovine serum, L-glutamine (2 mM), penicillin (100 U/ml), and streptomycin (0.1 mg/ml). For determination of $IC_{50}$, cells were exposed continuously with varying concentrations of drug concentrations and MTT assays were performed at the end of the fourth day.

The drug sensitive human epidermoid carcinoma KB3-1 cell line (S. Aliyama et al., *Somatic Cell Mol. Genet.*, 11, 117 (1985)) and its vinblastine-selected multidrug-resistant variant KBV-1 cells (D. W. Shen et al., *Science*, 32, 643 (1986)) were provided by Dr. Michael Gottesmann (National Cancer Institute, Bethesda, ML). These cells were grown as monolayer cultures at in 5% $CO_2$ and maintained by regular passage in Dulbecco's minimal essential medium supplemented with 10% heat inactivated fetal bovine serum. KBV-1 cells were similarly maintained except they were grown in the presence of 1 μg/ml vinblastine.

C. Results

As shown on Table 1, comparison of compounds 10–16 with Hoechst 33342 (1) as inhibitors of topoisomerase I demonstrated that several of these trisbenzimidazoles had similar potency.

TABLE 1

Topoisomerase I-mediated DNA Cleavage and Cytotoxicity of Bis- and Trisbenzimidazoles

| Compound | Topo I-mediated DNA cleavage[b] | Cytotoxicity $IC_{50}$[a] (μM) Cell Lines | | | |
|---|---|---|---|---|---|
| | | RPMI | CPT-K5 | KB3-1 | KBV-1 |
| Hoechst 33342 | 1 | 0.03 | 0.9 | 0.01 | 1.2 |
| 10 | 1.1 | 14 | 28 | N.D. | N.D. |
| 11 | 1 | >25[c] | >25[c] | N.D. | N.D. |
| 12 | 100 | 7.6 | 20 | N.D. | N.D. |
| 13 | 2 | 0.09 | 0.58 | 0.58 | 0.35 |
| 14 | 3.3 | 0.16 | 5.8 | 0.05 | 0.09 |
| 15 | 2 | 0.035 | 2.5 | 0.02 | 0.02 |
| 16 | 2 | 0.035 | 2.5 | 0.02 | 0.01 |
| 19 | 1000 | >25[c] | N.D. | N.D. | N.D. |

[a]$IC_{50}$ has been calculated after 4 days of continuous drug exposure.
N.D. = Not determined.
[b]Topoisomerase I cleavage values are reported as REC, Relative Effective Concentration, i.e. concentrations relative to Hoechst 33342, whose value is arbitrarily assumed as 1, that are able to produce the same cleavage on the plasmid DNA in the presence of calf thymus topoisomerase I. Cleavage is calculated from the intensity of the strongest Hoechst specific band.
[c]No indication of cytotoxicity were considered indicative of $IC_{50}$ values substantially greater than the highest doses assayed.

While 10 and 11 exhibited similar potency in their inhibition of topoisomerase I as observed with Hoechst 33342, both of these compounds failed to exhibit significant cytotoxicity towards the human lymphoblast cell line, RPMI 8402. However, this may be due to the inability of the pure compound to penetrate the target cells, which may be overcome by selection of a suitable carrier, such as liposomes. The 5-phenyl substituted trisbenzimidazole, 13, was approximately one-half as potent as Hoechst 33342 as a topoisomerase I inhibitor. In contrast to 10 and 11, however, it had significant cytotoxicity towards the human lymphoblast cell line, RPMI 8402 cells. As observed with Hoechst 33342. 13 was also effective against camptothecin-resistant CPT-K5 cells. The relative resistance of Hoechst 33342 and 13, expressed as the ratio of the $IC_{50}$ values of the resistant verses the drug sensitive cell line, is approximately 30 fold as compared to the relative resistance of camptothecin which is 2,500 fold, as reported by A. Y. Chen et al., *Cancer Res.*, 53, 1332 (1993). A similar effect was observed in another pair of cell lines; 13 has an $IC_{50}$ of 0.015 μg/ml in the human ovarian tumor cell line, A2780, relative to an $IC_{50}$ of 0.03 μg/ml in CPT-2000, a variant of A2780 selected for camptothecin-resistance and known to contain a mutant camptothecin-resistant topoisomerase I. The 5-n-propyl trisbenzimidazole derivative, 12, was much less active than either 10, 11, or 13 as an inhibitor of topoisomerase I. Its weak activity as a topoisomerase I inhibitor correlated with its weak cytotoxicity. The activity of several of these compounds were also evaluated using recombinant human topoisomerase I. Several of these analogs induced similar DNA cleavage in the presence of human topoisomerase I as compared to that observed with topoisomerase I isolated from calf thymus.

The cytotoxic activity of Hoechst 33342 and 13 was also evaluated against KB 3-1 and KB V-1 cells. The primary difference between these cell lines is in the degree to which human MDR1 (P-glycoprotein) is expressed. Recent studies have demonstrated that antineoplastic agents which are cationic at physiological pH are more likely to serve as substrates for MDR1 and, therefore, are likely to be less effective against cells that overexpress P-glycoprotein. In view of the fact that Hoechst 33342 is extensively protonated at physiological pH, it is not surprising that the $IC_{50}$ differs by approximately two-orders of magnitude for KB 3-1 as compared to KB V-1 cells, as reported by A. Y. Chen et al., *Adv. Pharmacol.*, 245, 29B (1994). In contrast to Hoechst 33342, there is little difference between the $IC_{50}$ values observed for 13 in these two cell lines. Thus, 13 appears not to be a substrate for human MDR1. This data indicate that these trisbenzimidazole derivatives may have significant chemotherapeutic advantages as compared to Hoechst 33342 or pibenzimol (Hoechst 33258), 2'-(4-hydroxyphenyl)-5-(4-methyl-1-piperazinyl)-2,5'-bi-1H-benzimidazole.

These data indicate that substitution of these trisbenzimidazole with a 5-Ar substituent can yield derivatives which are active as topoisomerase I inhibitors and cytotoxic to tumor cells. Trisbenzimidazoles substituted at the 5-position with either a 2-, 3-, or 4-pyridyl group, 14–16, were evaluated for their potency as topoisomerase I inhibitors and for cytotoxicity as summarized in Table 1. These analogs, similar to 13, have activity as topoisomerase I inhibitors. The 3- and 4-pyridyl analogs, 15 and 16, are somewhat more active than the 2-pyridyl derivative, 14, as topoisomerase I inhibitors as well as cytotoxic agents. As was observed with 13, these pyridyl-substituted tribenzimidazoles had similar cytotoxicity to KB 3-1 cells as well as to KB V-1 cells which overexpress MDR1. A principal advantage of these heteroaryl substituted trisbenzimidazoles as compared to Hoechst 33342 is their efficacy against cell lines which express MDR1.

All publications and patents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of inhibiting mammalian tumor cell growth comprising contacting a susceptible population of tumor cells with an effective growth-inhibiting amount of a compound of the formula:

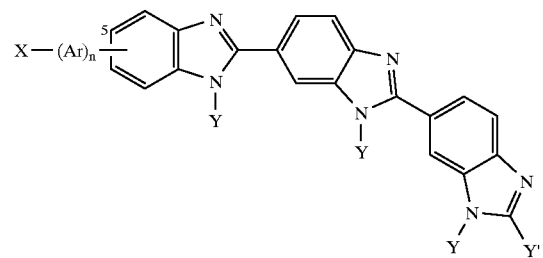

wherein Ar is $(C_6-C_{12})$aryl or (5- to 12-membered) heteroaryl comprising 1–3 N, S, or nonperoxide O, wherein N is unsubstituted or is substituted with $(C_1-C_4)$alkyl; X is H, CN, CHO OH, acetyl, $CF_3$, $O(C_1-C_4)$alkyl, $NO_2$ or $NH_2$; each of Y is H, $(C_1-C_4)$alkyl or aralkyl; Y' is H or $(C_1-C_4)$alkyl; n is 0–1; or a pharmaceutically acceptable salt thereof.

2. The method of claim 1 wherein n is 1 and Ar is at the 5-position.

3. The method of claim 1 wherein n is 1 and Ar is 5–6 membered heteroaryl comprising 1–2 N, S or non-peroxide O atoms.

4. The method of claim 3 wherein Ar is phenyl or pyridyl.

5. The method of claim 4 wherein pyridyl is 2-pyridyl, 3-pyridyl or 4-pyridyl.

6. The method of claim 4 or 5 wherein X is H.

7. The method of claim 6 wherein Y' is H.

8. The method of claim 4 or 5 wherein each Y is H.

9. The method of claim 1 wherein n is O and X is H, CHO or CN.

10. The method of claim 9 wherein Y' is H.

11. The method of claim 1, wherein the inhibition is carried out in vivo, by administering said compound to a mammal afflicted with cancer.

12. The method of claim 11 wherein the administration is oral.

13. The method of claim 11 wherein the administration is parenteral.

14. The method of claim 11 wherein the administration is intravenous.

15. The method of claim 11 wherein the administration is subcutaneous.

16. The method of claim 12 wherein the compound is administered in a unit dose form further comprising a pharmaceutically acceptable vehicle.

17. The method of claim 14 or claim 15 wherein the compound is administered in a unit dose form further comprising a pharmaceutically acceptable vehicle.

18. The method of claim 16 wherein the unit dose form is a ingestible tablet, buccal tablet, troche, capsule, elixir, suspension, syrup, or wafer.

19. The method of claim 18 wherein the unit dose form is an ingestible or buccal tablet.

20. The method of claim 17 wherein the unit dose form is a solution, dispersion or powder.

21. The method of claim 11 wherein the administration is intramuscular.

* * * * *